(12) United States Patent
Schwabe et al.

(10) Patent No.: US 6,218,461 B1
(45) Date of Patent: Apr. 17, 2001

(54) SILICONE COMPOSITION CURING AT ROOM TEMPERATURE AND THE USE THEREOF

(75) Inventors: Peter Schwabe, Leverkusen; Michael Freckmann, Köln; Klaus-Dieter Nehren, Dormagen, all of (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 0 days.

(21) Appl. No.: 09/255,958

(22) Filed: Feb. 23, 1999

(30) Foreign Application Priority Data

Feb. 28, 1998 (DE) ................................................. 198 08 557

(51) Int. Cl.⁷ ............................. C08L 83/04; C08L 83/06; A61K 6/10; B65D 85/84; C08G 77/06

(52) U.S. Cl. ........................... 524/588; 524/366; 524/378; 524/538; 524/606; 524/607; 524/788; 524/789; 524/860; 524/863; 524/864; 524/869; 523/109; 528/17; 528/33; 528/38; 206/63.5; 206/524.1; 106/35; 106/38.3; 106/38.35

(58) Field of Search ...................................... 524/456, 538, 524/588, 606, 607, 860, 863, 864, 869, 788, 789, 366, 378; 206/63.5, 524.1; 106/35, 38.3, 38.35; 528/17, 33, 38; 523/109

(56) References Cited

U.S. PATENT DOCUMENTS

| | | |
|---|---|---|
| 4,174,338 | * 11/1979 | Goller et al. . |
| 4,609,687 | 9/1986 | Schwabe et al. . |
| 4,891,400 | 1/1990 | Schwabe et al. . |
| 5,118,290 | 6/1992 | Müller et al. . |
| 5,750,589 | * 5/1998 | Zech et al. .......................... 523/109 |

FOREIGN PATENT DOCUMENTS

| | | | |
|---|---|---|---|
| 1153169 | 8/1963 | (DE) . | |
| 2644193 | 4/1978 | (DE) | ............................... C08L/83/04 |
| 3406233 | 8/1985 | (DE) | ............................... C08L/83/04 |
| 3636974 | 5/1988 | (DE) | ............................... C08G/18/10 |
| 4332037 | 3/1995 | (DE) | ............................... A61K/6/10 |
| 29 02 111 U | 7/1997 | (DE) | ............................... B65D/75/60 |
| 0219660 | 4/1987 | (EP) | ............................... A61K/6/10 |
| 0378806 | 7/1990 | (EP) | ............................... B05C/17/005 |

OTHER PUBLICATIONS

Ullmann's Encyclopedia of Industrial Chemistry, 5th Edition, vol. A8 (1987) p. 288.

Römpp Chemie Lexikon, 9th Edition, vol. 5, p. 3508.

\* cited by examiner

*Primary Examiner*—Robert Dawson
*Assistant Examiner*—Jeffrey B. Robertson
(74) *Attorney, Agent, or Firm*—Norris McLaughlin & Marcus

(57) ABSTRACT

A silicone composition curing at room temperature by condensation, which is suitable especially as a dental molding composition. The silicone composition consists of the a) base paste containing a filler and polyorganosiloxane having hydroxy groups, b) and the activator component containing in addition to crosslinking agent and catalyst also a polyaddition product with alkoxysilyl groups in the molecule. The base paste and activator component can be mixed uniformly together and can be offered with special advantage in double cartridges.

12 Claims, No Drawings

SILICONE COMPOSITION CURING AT ROOM TEMPERATURE AND THE USE THEREOF

The invention relates to a silicone composition curing by condensation at room temperature, composed of a filler and a base paste containing polyorganosiloxane having hydroxy groups, as well as an activator component containing crosslinking agent and a catalyst of an organometallic compound, and the use of the silicone composition.

The invention especially relates to a silicone composition curing by condensation at room temperature composed of a base paste containing filler and a polyorganosiloxane having hydroxy groups, as well as an activator component containing crosslinking agent and a catalyst of an organometallic compound, for use as a dental silicone casting composition.

Silicone stripping compositions are distinguished according whether they are crosslinked by condensation or by addition (R. Marxkors/H. Meiners, Taschenbuch der zahn ärzlichen Werkstoffkunde, Munich/Vienna: Carl Hanser Verlag, 1978; Ullmann's Encyclopedia of Industrial Chemistry, 5th ed., Weinheim; New York: VCH, Volume A8, 1987, 288).

The silicone casting compositions in the form of a two-component system consist—if they belong to those which crosslink by condensation—of a base paste containing polydimethyl silanols or other hydroxypolyorganosiloxanes and fillers as well as activator liquid or activator paste containing crosslinkers and catalyst for the polycondensation. After the two components are mixed shortly before use, the polydimethyl silanols react with the crosslinker consisting usually of silicic acid esters or other alkoxysilanes by condensation with chain lengthening, branching and crosslinking, and rubber-elastic materials very well suited for casting are formed. Silicone impression compositions crosslinking by condensation are disclosed, for example, in DE 1 153 169 B1, DE 26 44 193 A1, DE 34 06 233 A1, DE 36 36 974 A1 and DE 43 32 037 A1.

DE 1 153 169 B1 relates to a method of preparing elastomeric castings from two separate compositions in paste form, which are mixed together before curing at room temperature. One of the compositions contains hydroxy terminally blocked diorganopolysiloxane and crosslinkers, for example silicic acid ester or organohydrogen polysiloxanes, the other containing diorganopolysiloxane terminally blocked by triorganosiloxy groups and the condensation catalyst, such as dibutyl tin diacetate. The compositions are used mainly as impression or sealing compositions for technical, artistic or, especially, for dental purposes. It is disadvantageous that the composition containing the hydroxy terminally blocked diorganopolysiloxane and the crosslinker markedly loses its activity in storage.

DE 26 44 193 A1 has disclosed paste compositions for polyorganosiloxanes which can be vulcanized at room temperature, which contain, in addition to crosslinking substances and catalyst (hardening catalysts), 3 to 40 wt.-% of active hydrophilic silicic acid as thickening agent and, in some cases, up to 40 wt.-% of inactive fillers, such as quartz flour or titanium dioxide. Crosslinking substances are esters of silicic and polysilicic acids, alkyl alkoxy silanes, aryl alkoxy silanes or alkylalkanoyl oxysilanes. Their amount is 0.1–10 parts by weight with respect to the polyorganosiloxane. Catalysts are carboxylic acid metal salts, such as dibutyltin dilaurate, tin(II) octanoate, lead laurate, cobalt naphthenate and tetra-isopropyl titanate, or amines or amine salts, such as hexylamine, cyclohexylamine and butyl ammonium acetate. They are used in an amount between 0.1 and 10% of the polyorganosiloxane. The paste compositions are stable when stored in moisture-proof packages, and can, as well as the polyorganosiloxane pastes, be packed in tubes with a select opening diameters and proportioned by the length of the strands pressed from the tubes. The diameters of the tube openings are chosen so as to provide between 3 and 40 parts by weight of the paste compositions for each 100 parts by weight of the polyorganosiloxane pastes.

In DE 34 06 233 A1, finely divided fillers intended for silicone compositions in paste form which cure at room temperature by condensation or addition are described, whose particles are coated with paraffin oil, have an average particle size between 1 and 25 micrometers and can consist of calcium carbonate, cristobalite or quartz flour. The silicone compositions contain 30–90 weight-percent of the fillers and are used preferably in molding materials for dental purposes, a distinction being made between systems which crosslink by condensation and those which crosslink by addition. In the former case the liquid or paste activator components contain a carboxylic acid metal salt and a silicic acid ester, and the silicone compositions contain polyorganosiloxanes with two or more hydroxy groups in the molecule.

In DE 43 32 037 A1, a condensation-crosslinking silicone for molding in dentistry is proposed whose principal and secondary components are mixed in a 1:1 ratio and can be packaged in chambers of double cartridges in a 1:1 ratio by volume. The principal component consists of hydroxypolysiloxane, pyrogenic silicic acid, calcium carbonate, water and dibutyltin dilaurate, the secondary components consist of cristobalite, silicone oil and paraffin oil. This silicone, however, contains no crosslinking agent and therefore does not harden to a rubber-elastic material.

While in the case of addition-crosslinking silicone molding compositions, two-component systems in the form of pastes with good shelf life are known, which can be proportioned by weight or by volume, preferably in a 1:1 ratio (see, for example, EP 0 219 660 B1), this type contains no systems of crosslinking agents which are to be added to it and have good shelf life in the condensation-crosslinking silicone molding compositions.

The invention is therefore addressed to the problem of finding a silicone composition of the above-described kind which cures by condensation at room temperature and consists of both the paste and the activator component, wherein both components are stable in storage, can be proportioned in the desired ratio of admixture with one another and can be uniformly mixed together in any ratio. The activator component is to have a fluid-to-pasty consistency and is to permit the silicone composition to be offered in tubes, in tubular bags which are intended for use together with cartridges and are disclosed, for example, in DE 296 02 111 U1, and preferably in double cartridges. The silicone composition is to be suitable especially for use as a dental molding composition.

Double cartridges are two-chamber devices of the kind described, for example, in EP 0 378 806 B1 for mixing reactive components with one another and dispensing the paste mixtures obtained. Before use the stopper originally sealing the double cartridges is removed and inserted with the open dispensing end foremost into a static mixer. With double cartridges the correct ratio of admixture of the components and the uniformity of the mixed pastes can be achieved in a simple manner.

The silicone composition constituting the solution of the problem is characterized according to the invention in that the activator component additionally contains a polyaddition product with at least two alkoxysilyl groups in the molecule.

The term, polyaddition products, in the meaning of the invention are the products obtained as a result of a polyaddition. Polyaddition is a polymerization reaction in which polymers are built up by the frequently repeated addition of bisfunctional or polyfunctional educts or monomers (Römpp Chemie Lexikon, 9th ed., Stuttgart, New York: Georg Thieme Verlag, vol. 5, 3508).

The silicone composition according to the invention has proven especially valuable if the polyaddition product is one that contains ether, urethane, urea and alkoxysilyl groups, with a mainly linear molecular structure, exclusively aliphatically or cycloaliphatically bound ether, urethane and urea segments, and an average molecular weight of 800 to 20,000, a) a content of 25–90 wt.-% polyether groups,
b) a content of 0.5–10 wt.-% urethane groups (—NH—CO—O—),
c) a content of 0.5–10 wt.-% urea groups (—NH—CO—NH—), and
d) groups of the formula —NR—$(CH_2)_n$—$SiR^1R^2R^3$, wherein n represents the numbers 1–6, R hydrogen or —$(CH_2)_n$—$SiR^1R^2R^3$, $R^1$, $R^2$ and $R^3$ represent $C_1$–$C_4$ alkoxy independently of one another, the content of the alkoxysilyl groups —$SiR^1R^2R^3$ being 1 to 25 wt.-%.

Polyaddition products of the preferred kind and their preparation are disclosed, for example, in DE 36 36 974 A1. According to DE 36 36 974 A1, the polyaddition products described therein, containing ether, urethane and urea groups, are of a predominantly linear molecular structure with ether, urethane and urea segments bound exclusively (cyclo)aliphatically, and with an average molecular weight of 800 to 20,000, especially in the form of pastes, are used for making precise molds of jaws with teeth, with few teeth, and without teeth, and of plaster castings. For this purpose mixtures of the polyaddition products are prepared with a crosslinking agent, especially tetraethoxysilane, to which additional components are added, and are then used for making molding and duplicating compositions which cure at room temperature.

Surprisingly, by the concomitant use of the polyaddition products disclosed in DE 36 36 974 A1 in the activator component formed usually of crosslinking agent and catalytically active organometal compound, a silicone composition consisting of a base paste and activator component is created, in which the activator component is characterized by very good resistance to hydrolysis and stability in storage. The consistence of the activator component can be made to be from fluid to pasty, as required. The base paste and activator component can be measured out precisely both manually and automatically, and can be mixed uniformly together in any ratio, so that the silicone composition of the invention can advantageously be offered in packages permitting automatic measurement, proportioning and mixing.

For the silicone composition of the invention, an activator component has proven to be especially suitable which contains 10–90 weight-percent, preferably 30–50 wt.-%, of the polyaddition product. The amount of polyaddition product depends on the desired consistency of the activator component, which can be fluid to pasty as required. The desired consistency will depend on the form in which the silicone composition adapted to practical requirements is offered.

Crosslinker and catalyst form the additional components of the activator component. Any of the silicic acid esters and other alkoxysilanes known for this purpose can be used. Preferred are alkoxysilanes having 1 to 16 carbon atoms in the alkoxy moiety, which if desired can also contain ethylenically unsaturated groups in the molecule, such as vinyl trimethoxysilane, for example.

Suitable catalysts are the organic tin, organic titanium and organic zirconium compounds known for this purpose, especially dibutyltin and dioctyltin oxide and dibutyltin dilaurate.

The concomitant use of inorganic fillers, such as silica, in the activator component is possible, but not absolutely necessary.

The composition of the base paste is not special, and corresponds to the known silicone compositions of the condensation crosslinking type. In addition to the polyorganosiloxane containing hydroxy groups, the base paste additionally contains fillers known in themselves, for example quartz, cristobalite, calcium carbonate, sodium silicate, calcium silicate and/or glass, in conventional amounts and particle size, and working adjuvants in some cases such as hydrogenated castor oil. A filler content of 5 to 50 wt.-% has proven especially desirable.

The silicone composition according to the invention is suitable for mold making, for embedments and coatings and for similar applications. Its use as a dental molding composition proves to be especially advantageous.

For further explanation, a base paste (Examples 1 and 2) and an activator component (Example 3) are described below as examples suitable for the silicone composition of the invention. Example 4 relates to the judgment of the stability of the activator component in storage. Example 5 relates to the testing of the silicone compositions—silicone compositions I and II—mixed from base pastes A and B and the activator component, in accordance with ISO standard 4823:1992 in which the requirements of dental elastomeric molding compositions are laid down.

EXAMPLE 1

Base Paste A

In a vacuum planetary mixer the following were combined in the order given: 20 wt.-% of polydimethylsiloxane containing hydroxy groups, with a viscosity of 5000 mPa.s at 23° C., 51 wt.-% of polydimethylsiloxane containing hydroxy groups, with a viscosity of 1000 mpa.s at 23° C., 14 wt.-% of calcium silicate, 4 wt.-% of pyrogenic silicic acid and 1 wt.-% of inorganic pigment, and mixed together at 50 rpm for 30 minutes at room temperature and normal pressure to form a paste. Then the paste was degassed in a vacuum for another five minutes.

The finished paste is then packed a) in tubes, b) in tubular bags, and c) in one of the two chambers of double cartridges.

EXAMPLE 2

Base Paste B

In a vacuum planetary mixer the following were combined in the order given: 75 wt.-% of polydimethylsiloxane containing hydroxy groups, with a viscosity of 2000 mPa.s at 23° C., 20 wt.-% of a mixture of sodium silicate and calcium silicate, 4 wt.-% of hydrogenated castor oil, and 1 wt.-% of inorganic pigment, and mixed together at room temperature and normal pressure at 50 rpm for 30 minutes to form a paste. Then the paste is degassed in a vacuum for another 5 minutes.

The finished paste is then packed a) in tubes, b) in tubular bags, and c) in one of the two chambers of double cartridges.

EXAMPLE 3

Activator Component

As described in DE 36 36 974 A1, Example 3, a polyaddition product with a content of alkoxysilyl groups of 5.96 wt.-% is produced from a polyether prepared from propylene oxide, ethylene oxide and propylene glycol, isophorone diisocyanate, tin octanoate and 3-aminotriethoxysilane. 72.5 wt.-% of the polyaddition product is mixed uniformly with 27.5 wt.-% of a substance prepared from vinyl trimethoxysilane and dibutyltin oxide by heating for one hour at 120° C. with refluxing, followed by cooling. The activator component thus obtained is packed a) in tubes, b) in tubular bags, and c) in the second chambers of double cartridges whose first chambers already contain the base paste A or base paste B.

EXAMPLE 4

Stability in Storage

To judge stability in storage, the base pastes A and B and the activator component are mixed together a) immediately after packing and b) after the package has been stored at room temperature and 80% atmospheric humidity, in a ratio of 4:1 by volume, and the total processing times of the silicone compositions obtained are determined. The total processing times amount to: a) 2 minutes and b) 2.15 minutes; that is to say, the effectiveness of the activator component is virtually unaffected by storage.

EXAMPLE 5

Testing according to the standard ISO 4823:1992

The silicone compositions I and II are prepared by mixing 4 volume-parts of the base pastes A and B each with 1 volume-part of the activator component and tested according to the standard ISO 4823:1992. The results of the testing for consistency, total processing time, deformation under pressure, return to shape after deformation, and linear dimensional change are given in the table.

TABLE

| Test (ISO 4823:1992) | Silicone Composition I | Silicone Composition II |
|---|---|---|
| Consistency/disk diameter (mm) | 37.5 | 37.0 |
| Total processing time (s) | 120 | 120 |
| Deformation under pressure | 6.9 | 8.6 |
| Recovery of shape after deformation | 99.4 | 98.5 |
| Linear dimensional change | 0.99 | 0.92 |

What is claimed is:

1. Silicone composition curable at room temperature by condensation, composed of a) a base paste containing a filler and a polyorganosiloxane containing hydroxy groups and b) an activator component containing a crosslinking agent and a catalyst of an organic metal compound, wherein the activator component additionally contains a polyaddition product with at least two alkoxysilyl groups in the molecule.

2. Silicone composition according to claim 1, wherein the polyaddition product is a polyaddition product containing ether, urethane, urea and alkoxysilyl groups, with a predominantly linear molecule structure, exclusively aliphatically or cycloaliphatically bound ether, urethane and urea segments and an average molecular weight Mn of 800–20,000, a) a content of polyether groups of 25–90 wt.-%,
   b) a content of urethane groups (—NH—CO—O—) of 0.5–10 wt-%,
   c) a content of urea groups (—HN—CO—NH—) of 0.5–10 wt.-%,
   d) groups of the formula —NR—$(CH_2)_n$—$SiR^1R^2R^3$, wherein n represents the numerals 1–6, R hydrogen or —$(CH_2)_n$—$SiR^1R^2R^3$, $R^1$, $R^2$ and $R^3$ representing $C_1$ to $C_4$ alkoxy, the content of the alkoxyethyl groups $SiR^1R^2R^3$ amounting to 1 to 25 weight-percent.

3. Silicone composition according to claim 1 wherein the amount of polyaddition product in the activator component amounts to 10–90 weight-percent.

4. Silicone composition according to claim 3, wherein the amount of polyaddition product in the activator component amounts to 30–60 wt.-%.

5. Silicone composition according to claim 1 wherein the activator component contains vinyltrimethoxysilane as crosslinking agent.

6. Silicone composition according to claim 1 wherein the activator component contains dibutyltin or dioctyltin oxide as catalyst.

7. Silicone composition according to claim 1 wherein the base paste contains 5 to 50 wt.-% of the filler.

8. Silicone composition according to claim 7 wherein the base paste contains calcium silicate as filler.

9. Silicone composition according to claim 1, wherein said base paste and activator component are packaged in tubes.

10. Silicone composition according to claim 1, wherein said base paste and activator component are packaged in tubular bags.

11. Silicone composition according to claim 1, wherein said base paste and activator component are packaged in double cartridges.

12. A dental molding composition comprising the silicone composition of claim 1.

* * * * *